(12) United States Patent
Rigby

(10) Patent No.: US 7,238,782 B2
(45) Date of Patent: Jul. 3, 2007

(54) COMPOSITIONS AND METHODS FOR REGULATING RNA STABILITY USING POLYPYRIMIDINE TRACT PROTEINS

(75) Inventor: William F. C. Rigby, Etna, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/389,947

(22) Filed: Mar. 27, 2006

(65) Prior Publication Data

US 2006/0160993 A1 Jul. 20, 2006

Related U.S. Application Data

(62) Division of application No. 10/497,838, filed as application No. PCT/US03/01623 on Jan. 17, 2003, now Pat. No. 7,022,487.

(60) Provisional application No. 60/437,779, filed on Jan. 2, 2003, provisional application No. 60/349,869, filed on Jan. 17, 2002.

(51) Int. Cl.
*C07K 14/00* (2006.01)
*G01N 33/53* (2006.01)
*C12P 21/06* (2006.01)

(52) U.S. Cl. .......... 530/350; 435/7.1; 435/69.1
(58) Field of Classification Search .......... None
See application file for complete search history.

(56) References Cited

OTHER PUBLICATIONS

Gil et al., "Characterization of cDNAs encoding the polypyrimidine tract-binding protein", Genes & Development 1992 5:1224-1236.
Markovtsov et al., "Cooperative Assembly of an hnRNP Complex Induced by a Tissue-Specific Homolog of Polypyrimidine Tract Binding Protein", Molecular and cellular Biology 2000 20(20):7463-7479.
Patton et al., "Characterization and molecular cloning of polypyrimidine tract-binding protein:a component of a complex necessary for a pre-mRNA splicing", Genes & Development 1991 5:1237-1251.
Strasburg et al., "Generation and initial analysis of more than 15,000 full-length human and mouse cDNA sequences", Proc. Natl. Acad. Sci. USA 2002 99(26):16899-16903.

*Primary Examiner*—Robert B. Mondesi
(74) *Attorney, Agent, or Firm*—Licata & Tyrrell P.C.

(57) ABSTRACT

Compositions and methods for regulating CD154 gene expression are provided that rely on the interaction of polypyrimidine tract proteins with the 3'-untranslated region of CD154.

1 Claim, No Drawings

```
SEQUENCE LISTING

<160> NUMBER OF SEQ ID NOS: 11

<210> SEQ ID NO 1
<211> LENGTH: 197
<212> TYPE: PRT
<213> ORGANISM: Homo sapien

<400> SEQUENCE: 1

Met Asp Gly Ile Val Pro Asp Ile Ala Val Gly Thr Lys Arg Val Thr
1               5                   10                  15

Pro Gln Ser Leu Phe Ile Leu Phe Gly Val Tyr Gly Asp Val Gln Arg
            20                  25                  30

Val Lys Ile Leu Phe Asn Lys Lys Glu Asn Ala Leu Val Gln Met Ala
        35                  40                  45

Asp Gly Asn Gln Ala Gln Leu Ala Met Ser His Leu Asn Gly His Lys
    50                  55                  60

Leu His Gly Lys Pro Ile Arg Ile Thr Leu Ser Lys His Gln Asn Val
65                  70                  75                  80

Gln Leu Pro Arg Glu Gly Gln Glu Asp Gln Gly Leu Thr Lys Asp Tyr
                85                  90                  95

Gly Asn Ser Pro Leu His Arg Phe Lys Lys Pro Gly Ser Lys Asn Phe
            100                 105                 110

Gln Asn Ile Phe Pro Pro Ser Ala Thr Leu His Leu Ser Asn Ile Pro
        115                 120                 125

Pro Ser Val Ser Glu Glu Asp Leu Lys Val Leu Phe Ser Ser Asn Gly
    130                 135                 140

Gly Val Val Lys Gly Phe Lys Phe Phe Gln Lys Asp Arg Lys Met Ala
145                 150                 155                 160

Leu Ile Gln Met Gly Ser Val Glu Glu Ala Val Gln Ala Leu Ile Asp
                165                 170                 175

Leu His Asn His Asp Leu Gly Glu Asn His His Leu Arg Val Ser Phe
            180                 185                 190

Ser Lys Ser Thr Ile
        195

<210> SEQ ID NO 2
<211> LENGTH: 557
<212> TYPE: PRT
<213> ORGANISM: Homo sapien
```

<400> SEQUENCE: 2

```
Met Asp Gly Ile Val Pro Asp Ile Ala Val Gly Thr Lys Arg Gly Ser
 1               5                  10                  15

Asp Glu Leu Phe Ser Thr Cys Val Thr Asn Gly Pro Phe Ile Met Ser
                20                  25                  30

Ser Asn Ser Ala Ser Ala Ala Asn Gly Asn Asp Ser Lys Lys Phe Lys
            35                  40                  45

Gly Asp Ser Arg Ser Ala Gly Val Pro Ser Arg Val Ile His Ile Arg
        50                  55                  60

Lys Leu Pro Ile Asp Val Thr Glu Gly Glu Val Ile Ser Leu Gly Leu
 65                  70                  75                  80

Pro Phe Gly Lys Val Thr Asn Leu Leu Met Leu Lys Gly Lys Asn Gln
                85                  90                  95

Ala Phe Ile Glu Met Asn Thr Glu Glu Ala Ala Asn Thr Met Val Asn
                100                 105                 110

Tyr Tyr Thr Ser Val Thr Pro Val Leu Arg Gly Gln Pro Ile Tyr Ile
            115                 120                 125

Gln Phe Ser Asn His Lys Glu Leu Lys Thr Asp Ser Ser Pro Asn Gln
        130                 135                 140

Ala Arg Ala Gln Ala Ala Leu Gln Ala Val Asn Ser Val Gln Ser Gly
145                 150                 155                 160

Asn Leu Ala Leu Ala Ala Ser Ala Ala Val Asp Ala Gly Met Ala
                165                 170                 175

Met Ala Gly Gln Ser Pro Val Leu Arg Ile Ile Val Glu Asn Leu Phe
                180                 185                 190

Tyr Pro Val Thr Leu Asp Val Leu His Gln Ile Phe Ser Lys Phe Gly
            195                 200                 205

Thr Val Leu Lys Ile Ile Thr Phe Thr Lys Asn Asn Gln Phe Gln Ala
        210                 215                 220

Leu Leu Gln Tyr Ala Asp Pro Val Ser Ala Gln His Ala Lys Leu Ser
225                 230                 235                 240

Leu Asp Gly Gln Asn Ile Tyr Asn Ala Cys Cys Thr Leu Arg Ile Asp
                245                 250                 255

Phe Ser Lys Leu Thr Ser Leu Asn Val Lys Tyr Asn Asn Asp Lys Ser
                260                 265                 270

Arg Asp Tyr Thr Arg Pro Asp Leu Pro Ser Gly Asp Ser Gln Pro Ser
            275                 280                 285

Leu Asp Gln Thr Met Ala Ala Ala Phe Gly Ala Pro Gly Ile Ile Ser
        290                 295                 300

Ala Ser Pro Tyr Ala Gly Ala Gly Phe Pro Pro Thr Phe Ala Ile Pro
305                 310                 315                 320

Gln Ala Ala Gly Leu Ser Val Pro Asn Val His Gly Ala Leu Ala Pro
                325                 330                 335

Leu Ala Ile Pro Ser Ala Ala Ala Ala Ala Ala Gly Arg Ile
                340                 345                 350

Ala Ile Pro Gly Leu Ala Gly Ala Gly Asn Ser Val Leu Leu Val Ser
            355                 360                 365

Asn Leu Asn Pro Glu Arg Val Thr Pro Gln Ser Leu Phe Ile Leu Phe
        370                 375                 380

Gly Val Tyr Gly Asp Val Gln Arg Val Lys Ile Leu Phe Asn Lys Lys
385                 390                 395                 400

Glu Asn Ala Leu Val Gln Met Ala Asp Gly Asn Gln Ala Gln Leu Ala
                405                 410                 415
```

```
Met Ser His Leu Asn Gly His Lys Leu His Gly Lys Pro Ile Arg Ile
            420                 425                 430

Thr Leu Ser Lys His Gln Asn Val Gln Leu Pro Arg Glu Gly Gln Glu
        435                 440                 445

Asp Gln Gly Leu Thr Lys Asp Tyr Gly Asn Ser Pro Leu His Arg Phe
    450                 455                 460

Lys Lys Pro Gly Ser Lys Asn Phe Gln Asn Ile Phe Pro Pro Ser Ala
465                 470                 475                 480

Thr Leu His Leu Ser Asn Ile Pro Pro Ser Val Ser Glu Glu Asp Leu
                485                 490                 495

Lys Val Leu Phe Ser Ser Asn Gly Gly Val Val Lys Gly Phe Lys Phe
            500                 505                 510

Phe Gln Lys Asp Arg Lys Met Ala Leu Ile Gln Met Gly Ser Val Glu
        515                 520                 525

Glu Ala Val Gln Ala Leu Ile Asp Leu His Asn His Asp Leu Gly Glu
    530                 535                 540

Asn His His Leu Arg Val Ser Phe Ser Lys Ser Thr Ile
545                 550                 555

<210> SEQ ID NO 3
<211> LENGTH: 365
<212> TYPE: DNA
<213> ORGANISM: Homo sapien

<400> SEQUENCE: 3
caggctctag aacgtctaac acagtggaga accgaaaccc cccccccccc ccccgccacc      60
ctctcggaca gttattcatt ctctttcaat ctctctctct ccatctctct ctttcagtct     120
ctctctctca acctctttct tccaatctct cttttctcaat ctctctgttt cccttttgtca   180 gtctcttccc tcccccagtc tctcttctct cccccttttct aacacacaca cacacacaca   240
cacacacaca cacacacaca cacacacaca cacacacaca cacacagagt caggccgttg    300
ctagtcagtt ctcttctttc caccctgtcc ctatctctac cactatagat gagggtgagg    360
agtag                                                                365

<210> SEQ ID NO 4
<211> LENGTH: 5
<212> TYPE: RNA
<213> ORGANISM: Homo sapien

<400> SEQUENCE: 4 auuua                                                                  5

<210> SEQ ID NO 5
<211> LENGTH: 9
<212> TYPE: RNA
<213> ORGANISM: Homo sapien

<400> SEQUENCE: 5 uuauuuauu                                                              9

<210> SEQ ID NO 6
<211> LENGTH: 9
<212> TYPE: PRT
<213> ORGANISM: Bos taurus

<400> SEQUENCE: 6

Asp Tyr Gly Asn Ser Pro Leu His Arg
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cccgcggtct gctctgtgtg                                           20

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
aatctctcgg cggctaggtc act                                       23

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
ggtacttcgt ccacaaacac aactcc                                    26

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ggtggctccc gctgaattgg                                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ccgtcatcgt ctttccgtgc                                           20
```

COMPOSITIONS AND METHODS FOR REGULATING RNA STABILITY USING POLYPYRIMIDINE TRACT PROTEINS

INTRODUCTION

This application is a divisional of U.S. Ser. No. 10/497,838 filed Jun. 7, 2004, now U.S. Pat. No. 7,022,487 which is the U.S. National Phase of PCT/US2003/001623 filed Jan. 17, 2003, which claims priority to U.S. Provisional Application Nos. 60/437,779 filed Jan. 2, 2003 and 60/349,869 filed Jan. 17, 2002.

This invention was made in the course of research sponsored by the National Institutes of Health (NIH Grant No. AI34928). The U.S. government may have certain rights in this invention.

BACKGROUND OF THE INVENTION

The expression of CD154 (CD40 ligand) by activated T lymphocytes is critical in the development of humoral and cell-mediated immunity (Foy, et. al. (1996) *Annu. Rev. Immunol.* 14:591–617; Grewal and Flavell (1998) *Ann. Rev. Immunol.* 16:111–135; Noelle (1996) *Immunity* 4:415–419). The interaction of CD154 with its receptor, CD40, was first shown essential for B cell growth and differentiation and formation of germinal centers (Foy, et. al. (1996) *Annu. Rev. Immunol.* 14:591–617). This interaction is essential to numerous elements of cell-mediated immunity. In the absence of CD154, antigen presentation by dendritic cells and macrophages is profoundly impaired, as is macrophage-mediated killing of intracellular or extracellular pathogens (Grewal and Flavell (1998) supra; Noelle (1996) supra). Given the breadth of importance of CD154-CD40 interaction, it is not surprising that CD154 blockade retards the development and progression of immune responses in an array of transplantation and autoimmune disease models ranging from Systemic Lupus Erythematosus to Rheumatoid Arthritis to Multiple Sclerosis (Foy, et. al. (1996) supra; Grewal and Flavell (1998) supra).

The CD154 gene is located on the X chromosome, and belongs to the Tumor Necrosis Factor (TNF) gene family (Hollenbaugh, et. al. (1994) *Immunol. Rev.* 138:23–37). Study of CD154 expression chiefly involves CD4+ T lymphocytes, with the earliest studies showing that resting cells express little or no CD154 (Lane, et al. (1992) *Eur. J. Immunol.* 22:2573–2578; Nusslein, et al. (1996) *Eur. J. Immunol.* 26:846–850; Roy, et al. (1993) *J. Immunol.* 151:2497–2510). Activation of the T lymphocytes demonstrated that induction of CD154 expression was different from that of other cytokines. Signals (anti-CD3, mitogenic lectins) that triggered resting T cells to engage in high levels of proliferation and cytokine production would elicit very little (CD4+ T cells) or no (CD8+ T cells) expression on either mouse or human T cells (Lane, et al. (1992) supra; Nusslein, et al. (1996) supra; Roy, et al. (1993) supra). Optimal expression of CD154 was found to require pharmacologic stimulation provided by phorbol myristate acetate (PMA) and calcium ionophores such as ionomycin (Lane, et al. (1992) supra; Nusslein, et al. (1996) supra; Roy, et al. (1993) supra; Roy, et al. (1994) *Eur. J. Immunol.* 25:596–603). The induction of CD154 on T lymphocytes is blocked by concurrent treatment with cyclosporine and glucocorticoids; these effects are presumed to be transcriptional (Fuleihan, et al. (1994) *J. Clin. Invest.* 93:1315–1320; Roy, et al. (1993) supra) based on the presence of NF-AT sites in the CD154 promoter (Schubert, et al. (1995) *J. Biol. Chem.* 15:29264–29627). Since cyclosporine and glucocorticoids also inhibit cytokine production (Ashwell, et al. (1992) *Ann. Rev. Immunol.* 18:309–345; Sigal and Dumont (1992) *Ann. Rev. Immunol.* 10:519–60), this pathway does not account for the differential regulation of CD154 expression by T lymphocytes.

The expression of TNF-α is primarily regulated at the level of mRNA turnover and translation, conferred by adenine-uridine rich cis-acting elements (AURE) present in its 3'-untranslated region (Beutler and Kruys (1995) *J. Cardiovasc. Pharm.* 25:S1-8; Kontoyiannis, et al. (1999) *Immunity* 10:387–398; Shaw and Kamen (1986) *Cell* 46:659–669). CD154 mRNA is rapidly degraded in human peripheral blood T lymphocytes, with a half-life of approximately 30 minutes, similar to that of interleukin 2 (Ford, et al. (1999) *J. Immunol.* 162:4037–4044; Murakami, et al. (1999) *J. Immunol.* 163:2667–2673; Rigby, et al. (1999) *J. Immunol.* 163:4199–4206; Suarez, et al. (1997) *Eur. J. Immunol.* 27:2822–2829). CD154 and cytokine mRNA stability may be differentially regulated in activated T lymphocytes as evidenced by CD2 engagement by LFA-3 stabilizes CD154 mRNA without altering IL-2 mRNA stability (Murakami, et al. (1999) supra) and CD28 crosslinking increases cytokine (TNF-α, IL-2) production at the level of mRNA stability (Lindsten, et al. (1989) *Science* 244:339–343) while having minimal effect on CD154 expression (Ford, et al. (1999) supra).

Using human peripheral blood lymphocytes (PBL) it was observed that PMA or ionomycin treatment rapidly increased CD154 mRNA stability, even in the context of transcriptional inhibition (Rigby, et al. (1999) supra). In these studies, two major, p50 and p25, and two minor, p40 and p36, RNA binding proteins were shown to bind the CD154 3'-untranslated region. The binding of the p50 and p25 mapped to a polypyrimidine-rich region (~0.4 kb) that lacked an AURE. UV crosslinking studies demonstrated that the p50 and p25 directly contacted uridines and cytidines in this region. Signals which stabilized CD154 mRNA decreased p25 levels in both cytosolic and polysomal fractions, while a corresponding increase in p50 binding activity was observed (Rigby, et al. (1999) supra).

It has now been found that a novel cis-acting element in this polypyrimidine-rich region exists and regulates CD154 mRNA turnover through the relative levels of two polypyrimidine tract binding proteins.

SUMMARY OF THE INVENTION

One aspect of the present invention is a polypyrimidine tract protein isoform of SEQ ID NO:1.

Another aspect of the present invention is a method of increasing the stability of a ribonucleic acid operatively-linked to a cis-acting element of a CD154 3'-untranslated region. The method provides contacting a cell or tissue containing a ribonucleic acid sequence operatively-linked to a cis-acting element of a CD154 3'-untranslated region with an agent which increases the level or activity of a polypyrimidine tract protein, such as polypyrimidine tract protein (PTB) of SEQ ID NO:2, which when bound to the cis-acting element of the CD154 3'-untranslated region increases the stability of said ribonucleic acid sequence. The method further provides contacting the cell or tissue with an agent which decreases the level or activity of a polypyrimidine tract protein, such as polypyrimidine tract protein isoform (PTB-T) of SEQ ID NO:1, which when bound to the cis-acting element of the CD154 3'-untranslated region decreases the stability of said ribonucleic acid sequence.

Increasing the level or activity of PTB or decreasing the level or activity of PTB-T increases the stability of a ribonucleic acid operatively-linked to a cis-acting element of a CD154 3'-untranslated region in the cell or tissue. In a preferred embodiment, the cis-acting element is SEQ ID NO:3.

A further aspect of the present invention is a method of decreasing the stability of a ribonucleic acid operatively-linked to a cis-acting element of a CD154 3'-untranslated region. The method provides contacting a cell or tissue containing a ribonucleic acid sequence operatively-linked to a cis-acting element of a CD154 3'-untranslated region with an agent which decreases the level or activity of a polypyrimidine tract protein, such as polypyrimidine tract protein (PTB) of SEQ ID NO:2, which when bound to the cis-acting element of the CD154 3'-untranslated region increases the stability of said ribonucleic acid sequence. The method further provides contacting the cell or tissue with an agent which increases the level or activity of a polypyrimidine tract protein, such as polypyrimidine tract protein isoform (PTB-T) of SEQ ID NO:1, which when bound to the cis-acting element of the CD154 3'-untranslated region decreases the stability of said ribonucleic acid sequence. Decreasing the level or activity of PTB or increasing the level or activity of PTB-T decreases the stability of a ribonucleic acid operatively-linked to a cis-acting element of a CD154 3'-untranslated region in the cell or tissue. In a preferred embodiment, the cis-acting element is SEQ ID NO:3.

A still further aspect of the invention is a method of preventing or treating allograft rejection. The method provides administering to a subject in need of an allograft transplant an agent which decreases the level or activity of a polypyrimidine tract protein, such as polypyrimidine tract protein (PTB) of SEQ ID NO:2, which when bound to the cis-acting element of the CD154 3'-untranslated region increases the stability of the CD154 mRNA. The method further provides administering to a subject in need of an allograft transplant an agent which increases the level or activity of a polypyrimidine tract protein, such as polypyrimidine tract protein (PTB-T) of SEQ ID NO:1, which when bound to the cis-acting element of the CD154 3'-untranslated region decreases the stability of the CD154 mRNA. Decreasing the level or activity of PTB or increasing the level or activity of PTB-T decreases the stability of CD154 mRNA thereby preventing or treating allograft rejection.

A further aspect of the invention is a method of inhibiting CD40 activation. The method provides administering to a subject with a disorder associated with CD40 activation an effective amount of an agent which decreases the level or activity of a polypyrimidine tract protein, such as polypyrimidine tract protein (PTB) of SEQ ID NO:2, which when bound to the cis-acting element of the CD154 3'-untranslated region increases the stability of the CD154 mRNA. The method further provides administering to a subject with a disorder associated with CD40 activation an effective amount of an agent which increases the level or activity of a polypyrimidine tract protein, such as polypyrimidine tract protein (PTB-T) of SEQ ID NO:1, which when bound to the cis-acting element of the CD154 3'-untranslated region decreases the stability of the CD154 mRNA. Decreasing the level or activity of PTB or increasing the level or activity of PTB-T decreases the stability of CD154 mRNA thereby inhibiting CD40 activation.

Another aspect of the invention provides a method of identifying an agent which modulates the level or activity of a polypyrimidine tract protein. The method provides contacting a test cell containing a cis-acting element of CD154 3'-untranslated region of SEQ ID NO:3 operatively-linked to a nucleic acid sequence encoding a reporter, with an agent and detecting the expression of the reporter gene in the test cell in the absence and presence of said agent. Agents which decrease the expression of the reporter are indicative of agents which decrease the level or activity of PTB or increase the level or activity of PTB-T. Such agents are useful for preventing or treating allograft rejection and inhibiting CD40 activation. Agents which decrease the expression of the reporter are indicative of agents which increase the level or activity of PTB or decrease the level or activity of PTB-T.

These and other aspects of the present invention are set forth in more detail in the following description of the invention.

DETAILED DESCRIPTION OF THE INVENTION

Two RNA binding proteins that bind to the 3'-untranslated region (3'-UTR) of the CD154 ligand gene have now been identified. These two binding proteins are referred to as polypyrimidine tract binding proteins as the sequence to which they bind is rich in polypyrimidine. One of these proteins was identified as polypyrimidine tract binding protein or PTB (SEQ ID NO:2), also known as hnRNP I, and has now been shown to correspond to the cytoplasmic p50 CD154 3'-UTR binding protein. The other protein, which corresponds to p25, is a novel alternatively spliced isoform of PTB and is known as PTB-T (SEQ ID NO:1). By binding to polypyrimidine-rich sequences in the 3'-UTR of CD154, PTB-T influences the levels of CD40 ligand that are produced. In contrast, PTB competes with PTB-T for binding sites in the 3'-UTR of CD40 ligand, regulating CD40 ligand expression at a post-transcriptional level. Regulation of the level or activity of PTB-T or PTB by pharmacologic stimuli is contemplated as a useful tool in the treatment of autoimmune diseases and allograft rejection.

Experiments were performed to characterize, purify and identify polypyrimidine tract binding proteins as CD154 3'-UTR binding proteins. Excluding a ~0.3 kb insert (nucleotides 1 to 292) immediately distal to the translational stop site, the human and murine CD154 3'-UTR exhibit ~70% nucleotide identity between nucleotides 293 and 986. This level of conservation is similar to that seen in the TNF-α 3'-UTR (67%), which plays a dominant role in regulating its expression (Beutler and Kruys (1995) *J. Cardiovasc. Pharm.* 25:S1-8; Kontoyiannis, et al. (1999) supra). This conserved portion of the CD154 3'-UTR is distinguished by the presence of CU-rich and polycytidine sequences, as well as a CA dinucleotide repeat. Though CD154 mRNA stability is comparable to IL-2 (Rigby, et al. (1999) supra), it lacks the multiple AU-rich elements (AURE) seen in human TNF-α (9 AUUUA; SEQ ID NO:4) and IL-2 (7 AUUUA; SEQ ID NO:4) that occur within 500 nucleotides of the translational stop codon. Rather, the conserved portion of the human CD154 3'-UTR has a single distal AURE (UUAUUUAUU; SEQ ID NO:5) at nucleotides 951 to 959 in a context capable of destabilizing some, but not all, mRNA (Lagnado, et al. (1994) *Mol. Cell. Biol.* 14:7984–7995; Zubiaga, et al. (1995) *Mol. Cell. Biol.* 15:2219–2230).

Previous UV crosslinking studies identified RNA binding proteins with Mr of 50, 40, 36 and 25 kD in human peripheral blood lymphocyte (PBL) cytosols that directly contacted uridines and/or cytidines in the conserved region (nucleotides 293 to 986) of the human CD154 3'-UTR (Rigby, et al. (1999) supra). A similar pattern of CD154 3'-UTR binding was seen in ammonium sulfate (50%) precipitates of calf thymus (CT) nuclear extracts relative to cytosols from activated human PBL and the Jurkat human T lymphocyte line. Each extract contained, to slightly varying degrees, the four major proteins previously shown to directly contact radiolabeled [$^{32}$P]-UTP full-length CD154 3'-UTR. The p50, p40, and p25 binding activities mapped to the polypyrimidine-rich region (nucleotides 468 to 835) defined by the BstNI-HphI restriction enzyme sites in the human CD154 3'-UTR cDNA. Deletion of nucleotides 483 to 814 resulted in loss of p50, p40 and p25 binding in Jurkat cytosol and calf thymus extract. Activated human PBL cytosols also clearly demonstrate reduced p25 binding activity with this RNA transcript, however the decrease in p50 and p40 are obscured by the binding of additional proteins of slightly different Mr. These results demonstrate that calf thymus nuclear extracts, Jurkat cells, and PBL exhibit identical patterns (p50, p40, p25) of binding to the polypyrimidine-rich portion of the human CD154 3'-UTR.

The p50 and p25 binding proteins were purified from the 50% ammonium sulfate fraction of calf thymus nuclear extract by column chromatography for their ability to bind to radiolabeled nucleotides 468 to 835 in the CD154 3'-UTR. No significant binding to DEAE was noted; the flow through was applied to a carboxymethylcellulose (CMC) column. The p50 and p25 binding activity eluted from the CMC column at 0.3–0.5 M NaCl, while the p40 binding activity was predominantly noted in the 0.1 M salt elution. The 0.3 M NaCl elution was subjected to polyuridine column chromatography, where the p25 eluted at a slightly lower salt (0.5 M) concentration relative to the p50 (1 M NaCl). The 0.5 and 1 M NaCl elutions were resolved by SDS-PAGE, with the p25 and p50 bands being excised after visualization with COOMASSIE® blue staining. The p50 binding protein was identified by MALDI-TOF mass spectrometry as polypyrimidine tract binding protein (PTB), also known as hnRNP I (Garcia-Blanco, et al. (1989) *Genes Dev.* 3:1874–1886; Ghetti, et al. (1992) *Nucleic Acids Res.* 20:3671–3678; Gil, et al. (1991) *Genes Dev.* 5:1224–1236; Patton, et al. (1991) *Genes Dev.* 5:1237–1251). In contrast, the p25 could not be identified using this method or by N-terminal sequencing, the latter indicating that the amino terminus was blocked. Internal sequencing provided a nonapeptide (Asp-Tyr-Gly-Asn-Ser-Pro-Leu-His-Arg; SEQ ID NO:6) with 100% identity to amino acids 432 to 440 present in the third RNA Recognition Motif (RRM)-type RNA binding domain in human PTB (Garcia-Blanco, et al. (1989) supra; Patton, et al. (1991) supra).

Coordinate RNA binding assay and immunoblotting with the anti-PTB monoclonal antibody BB7 (Chou, et al. (2000) *Mol. Cell.* 5:949–957) demonstrated reactivity of the p50 and p25 binding proteins in the crude calf thymus nuclear extract as well as in the purified fractions. A minor 40 kD doublet was also detected by immunoblotting in calf thymus, one isoform of which copurified with the p50. A similar correlation of PTB-reactive proteins and CD154 3'-UTR binding activity was seen with Jurkat cytosols as well as polyribosome-enriched (polysomes) fractions purified by sucrose density gradients from PBL activated (6 hours) with either PHA or PMA/ionomycin. PMA/ionomycin activation of PBL, which induces CD154 mRNA stabilization, is associated with a loss of p25 binding activity, relative to PHA activation, from the polysomes while the p50 binding activity is increased and broadened (Rigby et al. (1999) supra). Immunoblotting demonstrated that the changes in binding activity were associated with loss of the immunoreactive p25 PTB isoform, and increased levels of PTB as well as emergence of a second, slightly larger isoform. Polysomes from PHA-activated PBL, in which CD154 mRNA is unstable, exhibited both p50 and p25 binding activity and PTB immunoreactivity.

Following incubation of Jurkat cytosol or calf thymus extract with radiolabeled CD154 3'-UTR RNA and UV-crosslinking, immunoprecipitation for PTB and an irrelevant RNA binding protein (hnRNP A2) was performed. Anti-PTB antibody immunoprecipitated radiolabeled RNA-protein complexes with a Mr of 50, 40, 25 kD from both Jurkat cytosol and calf thymus nuclear extract, indicating that each of these proteins directly contacted the RNA and was related to PTB. Anti-hnRNP A2 immunoprecipitated little (calf thymus) or no (Jurkat cytosol) binding activity, demonstrating the specificity of the observed data. These data indicate that the p40 and p25 CD154 3'-UTR binding proteins are related to PTB. By the same criteria, the p36 binding activity, which exhibited different binding specificity, is unrelated to PTB.

The identification of the p50 and p25 as PTB or PTB-related proteins is consistent with the description of multiple PTB splice isoforms and related, but distinct gene products. PTB was originally defined by its regulation of alternative splicing. Full-length PTB consists of four RNA recognition motif (RRM)-type RNA binding domains, and homodimerizes due to a region spanning the second RRM. Polypyrimidine tract binding activity is conferred by RRMs three and four (amino acids 324 to 531), particularly RRM three. Based on peptide sequence, binding activity, immunoreactivity and the inability to obtain N-terminal sequence, the data indicated that the p25 represented an alternatively spliced isoform of PTB. Using either oligo-d(T) or PTB 3'-UTR-specific primers for reverse transcription followed by PCR with primers specific for 5'- and 3'-UTR, RT-PCR amplification yielded a ~700 bp product. The predicted (1700 bp) band corresponding to PTB was not well visualized under these conditions, indicating preferential amplification of this smaller PCR product. This band was excised, cloned and sequenced, which confirmed it as a novel splice variant of PTB mRNA, with exons 3 though 9 deleted. The novel splice variant was confirmed by RT-PCR, cloning, and sequencing of three separate RNA samples, two from activated PBL from different donors, and one from the Jurkat T cell line. The splicing event results in a deletion of 360 amino acids, over 50% of wild-type PTB, to produce a polypeptide corresponding in size to the p25. In vitro translation yielded a protein of comparable size to the observed binding activity. Furthermore, immunoblotting with antisera specific for the N-terminal 13 amino acids of PTB demonstrated equivalent reactivity of the p25 to that seen with the BB7 antibody in PBL cytosol. These data provide that the p25 is an alternatively spliced isoform of PTB, distinctly different the p25 form of PTB resulting from proteolysis (Bothwell, et al. (1991) *J. Biol. Chem.* 266: 24657–63). Therefore, the p25 binding activity that correlated with mRNA turnover is encoded by a novel splice variant of PTB which retains most of RRM three and all of RRM four, the domains that confer polypyrimidine tract binding activity. The PTB isoform was named PTB-T lymphocyte, or PTB-T, referring to the cell type in which it was first identified. However, expression analysis of PTB-T mRNA or protein indicates that PTB-T is not restricted to lymphoid cells.

Addition of PMA/ionomycin to PHA-activated human peripheral blood T cells acutely increases CD154 mRNA stability, even in the context of RNA polymerase II inhibition. This effect is accompanied by decreased p25 binding and increased p50 binding in the cytosol (Rigby, et al. (1999) supra). With the identification of PTB and PTB-T as alternately spliced isoforms that bind the CD154 3'-UTR, immunoblot analysis was conducted to investigate binding. Cytosolic levels of PTB and PTB-T were not significantly affected by short term (4 hours) activation by a concentration of PHA that induced maximal proliferation and IL-2 production. Addition of PMA/ionomycin rapidly increased PTB levels in concert with a decline in PTB-T. RNA polymerase II inhibition by 5,6-di-chloro-1-beta-D-ribofuranosylbenzimidazole (DRB) alone increased cytoplasmic PTB. This effect was further enhanced by PMA/ionomycin treatment, indicating that the effect of PMA/ionomycin was independent of de novo gene transcription. Thus, cytosolic levels of PTB-T correlate with an unstable CD154 mRNA. A corollary of these data is that while PHA activation induces proliferation and lymphokine production by human PBL, it does not confer stabilization of CD154 mRNA. These data account for the inability to detect CD154 expression in the absence of PMA/ionomycin treatment. This inability of PHA activation to alter the relative cytoplasmic levels of PTB-T/PTB was maintained for at least the first 16 hours. With prolonged PHA activation (48 hours), a decline in cytosolic PTB-T was observed, consistent with reports that CD154 mRNA stability increases with prolonged T cell activation.

Chimeric reporter gene constructs were used to analyze the role of CD154 3'-UTR cis-acting elements in post-transcriptional gene regulation in vivo to avoid non-specific toxicity and effects of transcriptional inhibitors on mRNA stability. Firefly luciferase reporter constructs pcDNA3.1/LUC and pcDNA3.1/LUC/CD154 104–986 were generated, in which the CMV immediate early promoter drives transcription of a luciferase mRNA lacking or containing the conserved portion of the human CD154 3'-UTR. In the Jurkat human T cell line, the presence of the CD154 3'-UTR reduced luciferase expression to 34% of that seen with cells transfected with identical reporter gene plasmids lacking this sequence. A comparable level of inhibition of luciferase activity was conferred by the CD154 3'-UTR in transient transfection of HeLa cells. In each cell type, the level of inhibition of luciferase activity conferred by the CD154 3'-UTR was statistically significant (p<0.001). The level of inhibition of luciferase activity was equivalent to that seen with luciferase reporter constructs containing six reiterated AUUUA (SEQ ID NO:4) pentamers in their 3'-UTR. Thus, the CD154 3'-UTR contains sequences that modulate luciferase reporter gene expression in a promoter-independent manner to the same extent as an AURE.

CD154 3'-UTR-regulated luciferase reporter gene expression in transiently transfected Jurkat T lymphocytes was examined. Following transfection with the pcDNA3.1/LUC and pcDNA3.1/LUC/CD154 104–986 expression vectors, total cellular RNA was extracted and analyzed by northern blot. The presence of the CD154 3'-UTR reduced accumulation of luciferase mRNA by 60%. This effect was comparable to the magnitude (50%) of the CD154 3'-UTR-dependent reduction in luciferase activity measured at the same time as the RNA extraction. These data demonstrated a direct relationship between mRNA accumulation and luciferase expression. In five separate experiments, the effect of the CD154 3'-UTR on luciferase mRNA accumulation was measured by real time quantitative RT-PCR. The level of CD154 3$^1$-UTR-dependent reduction in luciferase mRNA accumulation was comparable to that seen by northern blot analysis. Thus, equivalent patterns of CD154 3'-UTR-dependent changes in luciferase mRNA accumulation were shown using distinct techniques. The parallel between the magnitude of the effect of the CD154 3'-UTR on luciferase mRNA and luciferase activity indicates a change in mRNA stability, since the rate of transcription from each promoter should be equivalent. This is consistent with reports demonstrating the instability of CD154 mRNA (Ford, et al. (1999) supra; Murakami, et al. (1999) supra; Rigby, et al. (1999) supra; Suarez, et al. (1997) supra) and the role of the 3'-UTR in regulating mRNA turnover (Ross (1988) *Mol. Biol. Med.* 5:1–14).

Deletion analysis was performed to map the cis-acting element in the CD154 3'-UTR. Removal of the entire polypyrimidine-rich region in the 485–814 deletion construct resulted in a loss of inhibition of luciferase activity. Constructs with smaller deletions of the polypyrimidine-rich region all demonstrated inhibitory activity. Deletion of the polycytidine sequence, CU dinucleotide repeat-rich region (nucleotides 560 to 600) or even deletion of >75% of the CU-rich region (nucleotides 540 to 690) with the 468–549 deletion, 557–647 deletion, or 585–690 deletion reporter constructs, still resulted in reduced luciferase expression in a 3'-UTR-dependent manner. Finally, the polypyrimidine-rich region alone (nucleotides 474 to 835) of human CD154 3'-UTR reduced luciferase activity to a comparable degree to that seen with nucleotides 104 to 986. These effects were statistically significant (p<0.0005).

When analyzed by transient transfection of Jurkat cells, both the CD154 3'-UTR and the polypyrimidine-rich region alone (474 to 835) were capable at reducing mRNA accumulation; deletion of this region resulted in loss of inhibition. Thus, the polypyrimidine-rich region of human CD154 3'-UTR is both necessary and sufficient to reduce both luciferase activity and steady state luciferase mRNA accumulation in a 3'-UTR-dependent manner. Importantly, this region (nucleotides 474 to 835) lacks an AURE, indicating that this effect on reporter gene mRNA levels is mediated by a cis-acting element.

A tetracycline-responsive luciferase (pTRE-luc) vector that either lacked or contained the CD154 3'-UTR was generated to conduct mRNA stability experiments in the absence of RNA polymerase II inhibitors. HeLa cells (TET-OFF™) were transiently transfected with these constructs and transcription was controlled with doxycycline. mRNA stability was evaluated by quantitative RT-PCR analysis. The presence of the CD154 3'-UTR resulted in a greater than two-fold increase in the rate of luciferase mRNA decay. This effect of the CD154 3'-UTR required the presence of the polypyrimidine-rich region; deletion of nucleotides 485 to 814 exhibited increased mRNA stability relative to the CD154 3'-UTR vector. Interestingly, the 485 to 814 deletion construct demonstrated increased mRNA stability relative to the control vector alone in two experiments. This finding is consistent with augmented mRNA accumulation relative to the luciferase control seen with transient transfection of Jurkat T cells. Thus, the retained AURE (UUAUUUAUU; SEQ ID NO:5) in the 485 to 814 deletion construct had no inhibitory effect on mRNA accumulation, indicating it lacked activity in this context.

Overexpression of PTB or PTB-T in a transient transfection assay was performed to determine the differential regulation of CD154 3'-UTR-dependent gene expression. In the Jurkat human T cell line, transfection of an expression vector encoding PTB increased CD154 3'-UTR-dependent gene expression relative to empty vector controls. In contrast, transfection of an expression vector encoding PTB-T markedly reduced luciferase activity in a CD154 3'-UTR-dependent manner. These effects were statistically significant. A similar, statistically significant effect of PTB-T overexpression was seen in HeLa cells. These data are consistent with the interpretation that levels of cytoplasmic PTB-T were limiting in both cell types. No effect of PTB overexpression was seen in HeLa cells, indicating the possibility that PTB levels in these cells were not limiting. The presence of the polypyrimidine-rich region in the luciferase 3'-UTR was both necessary and sufficient to confer the inhibitory effect of PTB-T transfection on luciferase expression.

A similar pattern was seen in transient transfection of purified human CD4+ T lymphocytes. Following transfection, luciferase activity in CD4+ T cells was measured after 6 hours either without (basal) or with PMA/ionomycin stimulation. The presence of the CD154 3'-UTR reduced luciferase activity in both HeLa and Jurkat cell lines under both basal and stimulated conditions. Moreover, in primary human CD4+ T cells, PTB and PTB-T overexpression differentially affected luciferase expression, in a CD154 3'-UTR-dependent manner. When expressed as a function of their effect on CD154 3'-UTR-dependent gene expression from four experiments, the inhibitory effect of PTB-T was statistically significant. The selectivity of the effect of PTB-T transfection for the CD154 3'-UTR was demonstrable through its lack of effect on reporter gene activity derived from the pcDNA3.1/LUC control. Furthermore, no effect on pRL-null-derived *Renilla* luciferase activity was seen, which was used to control for transfection efficiency in each experiment. In separate experiments, it was demonstrated that, as in Jurkat cells, the effect of PTB-T on luciferase expression in normal human CD4+ T lymphocytes was conferred by nucleotides 468 to 835. PTB-T reduced luciferase expression by pcDNA3.1/LUC/CD154 104–986 by 38% relative to controls. Transfection of PTB-T cDNA had a greater effect (58% inhibition) of luciferase expression by pcDNA3.1/LUC/CD154 468–835 (n=4). Together, these data show that PTB-T, and in some instances, PTB, regulated CD154 gene expression in both normal human T cells and cell lines solely through their interaction with the polypyrimidine-rich region found in the 3'-UTR.

As demonstrated herein, the CD154 3'-UTR contains a cis-acting element which decreases reporter gene expression at the level of mRNA accumulation in vivo. The polypyrimidine-rich region of CD154 3'-UTR was sufficient to reduce reporter gene expression indicating the presence of a cis-acting element in this region that regulates mRNA turnover. This same region also binds both PTB (SEQ ID NO:2) and a novel splice isoform now identified as PTB-T (SEQ ID NO:1), which both function as trans-acting factors to regulate the function of the cis-acting element. Therefore, both PTB and PTB-T, by binding to the polypyrimidine-rich region of human CD154 3'-UTR, play critical roles in regulating CD154 expression in vivo. Furthermore, it is believed that as cytoplasmic levels of PTB increase, PTB-T is displaced due to the higher avidity of dimeric PTB for binding to the CD154 3'-UTR. In contrast to PTB, PTB-T lacks the homodimerization domain that encompasses RRM two. Dimeric PTB may interact with the polypyrimidine-rich region of the CD154 3'-UTR at multiple sites and have a distinct effect on RNA structure relative to PTB-T, thus favoring CD154 mRNA stability. Therefore, a novel pathway that involves PTB and PTB-T has been identified that results in post-translational regulation of CD154 gene expression.

Accordingly, the present invention provides methods of modulating or regulating, in a cell or tissue, the stability of a ribonucleic acid (RNA) sequence operatively-linked to a cis-acting element of a CD154 3'-UTR via the binding of a polypyrimidine tract protein such as PTB, PTB-T or isoforms thereof (e.g., p40). These methods provide contacting the cell or tissue with an agent which modulates, regulates or alters the level or activity of a polypyrimidine tract protein thereby modulating or regulating the stability of an RNA sequence operatively-linked to a cis-acting of a CD154 3'-UTR. For illustrative purposes, PTB (SEQ ID NO:2) and PTB-T (SEQ ID NO:1) are used in the disclosure of the present of the invention, however, it should be understood that polypyrimidine tract proteins which have binding characteristics similar to PTB or PTB-T, e.g., p40, are also contemplated.

Methods of modulating or regulating the stability of an RNA sequence operatively-linked to a cis-acting element of a CD154 3'-UTR encompass both increasing and decreasing the stability of said RNA sequence. In one aspect of the invention, the stability of said RNA is increased by contacting the cell or tissue with an agent which increases or stimulates the level or activity of PTB (SEQ ID NO:2) or decreases or inhibits the level or activity of PTB-T (SEQ ID NO:1). In another aspect of the invention, the stability of said RNA is decreased by contacting a cell or tissue with an agent which decreases or inhibits the level or activity of PTB (SEQ ID NO:2) or increases or stimulates the level or activity of PTB-T (SEQ ID NO:1). The stability of said RNA by may determined using standard techniques such as western blot analysis of the translated product of the RNA sequence, northern blot analysis, reverse-transcriptase PCR, or other well-known methods for measuring RNA transcript levels. Regulation of the level or activity of PTB-T or PTB by pharmacological agents is contemplated as a useful tool in the treatment of autoimmune diseases and allograft rejection.

Accordingly, another aspect of the invention is a method of preventing or treating allograft rejection in a subject or mammalian recipient of a tissue graft or any mammal in need of a tissue graft. The method provides decreasing the stability of CD154 mRNA prior to, during, and/or after a tissue graft. The stability of the CD154 mRNA is decreased by administering to said subject an effective amount of an agent which decreases or inhibits the level or activity of PTB (SEQ ID NO:2) or increases or inhibits the level or activity of PTB-T (SEQ ID NO:1). Preferably, the subject is a primate, more preferably a higher primate, most preferably a human. In other embodiments, the subject may be another mammal in need of a tissue graft, particularly a mammal of commercial importance, or a companion animal or other animal of value. Thus, subjects also include, but are not limited to, sheep, horses, cattle, goats, pigs, dogs, cats, rabbits, guinea pigs, hamsters, rats and mice.

It is contemplated that the agent may be administered as a capsule, intramuscularly, intraperitoneally, subcutaneously, intradermally or applied locally to a wound site. It is also clear that the invention can be used with a skin graft procedure. The skin is a notoriously difficult tissue with which to achieve or maintain engraftment. A preferred route of administration for treating or preventing skin graft rejection is topical, subdermal, intradermal or subcutaneous, though systemic and other routes are also contemplated.

Another preferred route of administration includes direct application locally (by topical application, immersion or bath, or local injection) into the subject tissue bed, or to the graft tissue itself. High local concentrations of the agent, particularly in areas of lymphatic drainage, are expected to be particularly advantageous. Alternatively, the graft tissue may be transfected or transformed with a recombinant expression vector to overexpress PTB-T or inhibit the expression of PTB by antisense expression of PTB.

An effective amount of an agent which decreases the level or activity of PTB or increases the level or activity of PTB-T is an amount which decreases or inhibits the signs or symptoms of allograft rejection (e.g., edema, fever, and loss of graft function) and will be dependent on the nature of the agent. For example, an effective, non-toxic amount of an anti-PTB antagonistic antibody would generally be in the range of about 0.05 to 100 milligrams per kilogram body weight per day.

The method may be used with any type of tissue transplant or graft procedure, particularly procedures wherein the donor (grafted) tissue is affected by, or at risk of, failure or rejection by the subject's immune system. The donor tissue may be derived, by conventional means, from a volunteer or other living donor, or from a cadaveric donor. The donor tissue may also be artificial tissue, such as artificial skin products. Preferably, the donor is as histocompatible as practicable with the recipient host.

The donor tissue comprises an organ, a portion of an organ, such as a liver, a kidney or a heart, or a body part comprising multiple tissue types such as a joint, a hand, a foot, a myocutaneous flap or a finger. The donor tissue may further comprise a part, portion or biopsy of a donor organ or tissue; isolated or suspended cells, including cells withdrawn or excised from a donor host, cells maintained in primary culture, or an immortalized cell line; cells harboring exogenous genetic material, such as transfected or transformed host cells which have been (or are derived from ancestor cells which have been) engineered to include genetic material necessary for the production of a polypeptide of therapeutic value to the recipient host.

A further aspect of the invention is a method of inhibiting CD40 activation. The method provides decreasing the stability of CD154 mRNA in a subject suffering from a disorder associated with CD40 activation. The stability of the CD154 mRNA is decreased by administering to said subject an effective amount of an agent which decreases or inhibits the level or activity of PTB (SEQ ID NO:2) or increases or inhibits the level or activity of PTB-T (SEQ ID NO:1). An effective amount of an agent which decreases the level or activity of PTB or increases the level or activity of PTB-T is an amount which decreases or inhibits the signs or symptoms of CD40 activation (e.g., inflammation; renal disorder; or B cell, macrophage, or dendritic cell activation) and will be dependent on the nature of the agent. The subject may be a non-human or, preferably, a human animal. Disorders associated with CD40 activation include, but are not limited to, allergy (including anaphylaxis); atherosclerosis; autoimmune conditions including drug induced lupus, systemic lupus erythematosus, adult rheumatoid arthritis, juvenile rheumatoid arthritis, scleroderma, Sjogren's Syndrome, etc.; and viral diseases that involve B-cells, including Epstein-Barr infection, and retroviral infection including infection with a human immunodeficiency virus.

Because it has been suggested that B cell activation is associated with the induction of human immunodeficiency virus replication from latency, it may be desirable to decrease the stability of CD154 mRNA in HIV positive individuals who have not yet developed AIDS or ARC.

Agents useful in accordance with the methods provided herein include, but are not limited to, purified PTB or PTB-T protein, a recombinant expression vector expressing PTB or PTB-T, a recombinant expression vector expressing antisense PTB or PTB-T, antisense oligonucleotides to PTB or PTB-T, organic molecules, biomolecules including peptides, antibodies, saccharides, fatty acids, steroids, purines, pyrimidines, derivatives, structural analogs or combinations thereof.

An isolated or purified PTB or PTB-T protein for administration to a cell or tissue may be produced by various means. An isolated or purified protein is substantially free of cellular material or other contaminating proteins from the cell or tissue source from which the PTB or PTB-T protein is derived. To be substantially free of cellular material includes preparations of PTB or PTB-T protein in which the protein is separated from cellular components of the cells from which it is isolated or recombinantly produced. When the PTB or PTB-T protein is recombinantly produced, it is also preferably substantially free of culture medium.

Recombinant production of PTB or PTB-T typically involves generating a fusion protein such as a GST-PTB or GST-PTB-T fusion protein in which the PTB or PTB-T sequences are fused to the C-terminus of the GST sequences. Such fusion proteins can facilitate the purification of recombinant PTB or PTB-T. Alternatively, the fusion protein is a PTB or PTB-T protein containing a heterologous signal sequence at its N-terminus. In certain host cells (e.g., mammalian host cells), expression and/or secretion of PTB or PTB-T can be increased through use of a heterologous signal sequence. Preferably, a PTB or PTB-T chimeric or fusion protein of the invention is produced by standard recombinant DNA techniques. For example, DNA fragments coding for the different polypeptide sequences are ligated together in-frame in accordance with conventional techniques, for example by employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. Alternatively, the fusion gene may be synthesized by conventional techniques including automated DNA synthesizers or PCR amplification. PCR amplification of gene fragments may be carried out using anchor primers which give rise to complementary overhangs between two consecutive gene fragments which are subsequently annealed and reamplified to generate a chimeric gene sequence (see, e.g., Current Protocols in Molecular Biology, eds. Ausubel et al. John Wiley & Sons, 1992). Moreover, many expression vectors are commercially available that already encode a fusion moiety (e.g., a GST polypeptide). A PTB- or PTB-T-encoding nucleic acid can be cloned into such an expression vector such that the fusion moiety is linked in-frame to the PTB or PTB-T protein.

A recombinant expression vector comprises a nucleic acid sequence encoding PTB or PTB-T in a form suitable for expression of the nucleic acid sequence in a host cell, which means that the recombinant expression vector includes one or more regulatory sequences, selected on the basis of the host cells to be used for expression, which is operatively-linked to the nucleic acid sequence to be expressed. Within a recombinant expression vector, operatively-linked is intended to mean that the nucleotide sequence of interest is linked to the regulatory sequence(s) in a manner which allows for expression of the nucleotide sequence (e.g., in an in vitro transcription/translation system or in a host cell). A regulatory sequence is intended to include promoters, enhancers and other expression control elements (e.g., polyadenylation signals). Such regulatory sequences are described, for example, in Goeddel (1990) *Methods Enzy-* mol. 185:3–7. Regulatory sequences include those which direct constitutive expression of a nucleic acid sequence in many types of host cells and those which direct expression of the nucleotide sequence only in certain host cells (e.g., tissue-specific regulatory sequences). It will be appreciated by one of skill in the art that the design of the expression vector depends on such factors as the choice of the host cell to be transformed, the level of expression of protein desired, and the like. The expression vector may be introduced into a host cell to thereby produce proteins or peptides of PTB or PTB-T, isoforms of PTB or PTB-T, mutant forms of PTB or PTB-T proteins, fusion proteins, and the like.

A recombinant expression vector may be designed for expression of PTB or PTB-T proteins in prokaryotic or eukaryotic cells. For example, PTB or PTB-T proteins may be expressed in bacterial cells such as *E. coli*, insect cells (using baculovirus expression vectors), yeast cells or mammalian cells. Suitable host cells are discussed further in Goeddel (1990) supra. Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve to increase expression of recombinant protein; increase the solubility of the recombinant protein; and aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann, et al., (1988) *Gene* 69:301–315) and pET 1d (Studier, et al. (1990) *Methods Enzymol.* 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

The PTB or PTB-T expression vector may also encompass a yeast expression vector. Examples of vectors for expression in yeast *Saccharomyces cerevisiae* include pYepSec 1 (Baldari, et al. (1987) *EMBO J.* 6:229–234), pMFa (Kurjan and Herskowitz (1982) *Cell* 30:933–943), pJRY88 (Schultz, et al. (1987) *Gene* 54:113–123), pYES2 (INVITROGEN™ Corp., San Diego, Calif.), and picZ (INVITROGEN™ Corp., San Diego, Calif.).

Alternatively, PTB or PTB-T proteins may be expressed in insect cells using baculovirus expression vectors. Baculovirus vectors available for expression of proteins in cultured insect cells (e.g., Sf9 cells) include the pAc series (Smith, et al. (1983) *Mol. Cell Biol.* 3:2156–2165) and the pVL series (Lucklow and Summers (1989) *Virology* 170: 31–39).

Further, nucleic acid sequences encoding PTB or PTB-T are expressed in mammalian cells using a mammalian expression vector. As will be appreciated by one of skill in the art, PTB or PTB-T expression in mammalian cells provides a means of purifying the proteins as well as a means of modulating the endogenous levels of PTB or PTB-T proteins in a cell. Examples of mammalian expression vectors include any one of the well-known recombinant viral vectors, pCDM8 (Seed (1987) *Nature* 329:840) and pMT2PC (Kaufman, et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, et al. Molecular Cloning: A Laboratory Manual. $2^{nd}$ ed., Cold Spring Harbor Laboratory, Cold Spring Harbor Laboratory Press, Cold Spring Harbor, N.Y., 1989.

The recombinant mammalian expression vector may further be capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji, et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund, et al. (1985) *Science* 230:912–916), and mammary gland-specific promoters (e.g., milk whey promoter; U.S. Pat. No. 4,873,316 and EP 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

In addition to increasing the expression of PTB or PTB-T to modulate the levels of PTB or PTB-T present in the cell, PTB or PTB-T expression may be decreased to modulate the levels of PTB or PTB-T present in the cell. Thus, a recombinant expression vector harboring a nucleic acid sequence encoding PTB or PTB-T cloned into the expression vector in an antisense orientation is also provided. That is, the nucleic acid sequence encoding PTB or PTB-T is operatively-linked to a regulatory sequence in a manner which allows for expression (by transcription of the nucleic acid sequence) of an RNA molecule which is antisense to PTB or PTB-T mRNA. Regulatory sequences operatively-linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type-specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, et al. (1986) *Reviews-Trends in Genetics* Vol. 1(1).

Host cells into which a PTB or PTB-T nucleic acid sequence may be introduced, e.g., a PTB or PTB-T nucleic acid sequence within a vector (e.g., a recombinant expression vector) or a PTB or PTB-T nucleic acid sequence containing sequences which allow it to homologously recombined into a specific site of the host cell's genome, are further contemplated. The terms host cell and recombinant host cell are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example, a PTB or PTB-T protein may be expressed in bacterial cells such as *E. coli*, insect cells, yeast or mammalian cells (such as Chinese hamster ovary cells (CHO) or COS cells). Other suitable host cells are exemplified herein and are known to those skilled in the art.

Vector DNA may be introduced into prokaryotic or eukaryotic cells via conventional transformation or transfection techniques. As used herein, the terms transformation and transfection are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the nucleic acid sequence of interest. Preferred selectable markers include those which confer resistance to drugs, such as G418, hygromycin and methotrexate. Nucleic acid encoding a selectable marker can be introduced into a host cell on the same vector as that encoding a PTB or PTB-T protein or may be introduced on a separate vector. Cells stably transfected with the introduced nucleic acid may be identified by drug selection (e.g., cells that have incorporated the selectable marker gene will survive, while the other cells die). A host cell, such as a prokaryotic or eukaryotic host cell in culture, may be used to produce (i.e., express) a PTB or PTB-T protein.

The host cells may also be used to produce non-human transgenic animals. For example, a host cell is a fertilized oocyte or an embryonic stem cell into which PTB or PTB-T-coding sequences have been introduced. Such host cells may then be used to create non-human transgenic animals in which exogenous PTB or PTB-T sequences have been introduced into their genome or homologous recombinant animals in which endogenous PTB or PTB-T sequences have been altered. Such animals are useful for studying the function and/or activity of a PTB or PTB-T protein and for identifying and/or evaluating modulators of PTB or PTB-T activity. As used herein, a transgenic animal is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a homologous recombinant animal is a non-human animal, preferably a mammal, more preferably a mouse, in which an endogenous PTB or PTB-T gene has been altered by homologous recombination between the endogenous gene and an exogenous DNA molecule introduced into a cell of the animal, e.g., an embryonic cell of the animal, prior to development of the animal.

A transgenic animal may be created by introducing a PTB or PTB-T-encoding nucleic acid into the male pronuclei of a fertilized oocyte, e.g., by microinjection or retroviral infection, and allowing the oocyte to develop in a pseudopregnant female foster animal. Alternatively, a non-human homologue of a human PTB or PTB-T gene, such as a rat or mouse PTB or PTB-T gene, may be used as a transgene. Intronic sequences and polyadenylation signals may also be included in the transgene to increase the efficiency of expression of the transgene. A tissue-specific regulatory sequence(s) can be operatively-linked to a PTB or PTB-T transgene to direct expression of a PTB or PTB-T protein to particular cells. Methods for generating transgenic animals via embryo manipulation and microinjection, particularly animals such as mice, have become conventional in the art and are described, for example, in U.S. Pat. Nos. 4,736,866; 4,870,009; 4,873,191; and in Hogan, Manipulating the Mouse Embryo, (Cold Spring Harbor Laboratory Press, Cold Spring Harbor, N.Y., 1986). Similar methods are used for production of other transgenic animals. A transgenic founder animal may be identified based upon the presence of a PTB or PTB-T transgene in its genome and/or expression of PTB or PTB-T mRNA in tissues or cells of the animals. A transgenic founder animal can then be used to breed additional animals carrying the transgene. Moreover, transgenic animals carrying a transgene encoding a PTB or PTB-T protein may further be bred to other transgenic animals carrying other transgenes.

To create a homologous recombinant animal, a vector is prepared which contains at least a portion of a PTB or PTB-T gene into which a deletion, addition or substitution has been introduced to thereby alter, e.g., functionally disrupt, the PTB or PTB-T gene. The PTB or PTB-T gene may be a human gene or a non-human homologue of a human PTB or PTB-T gene. For example, a mouse PTB or PTB-T gene may be used to construct a homologous recombination nucleic acid molecule, e.g., a vector, suitable for altering an endogenous PTB or PTB-T gene in the mouse genome. The homologous recombination nucleic acid molecule may be designed such that, upon homologous recombination, the endogenous PTB or PTB-T gene is functionally disrupted (i.e., no longer encodes a functional protein; also referred to as a knock out vector). Alternatively, the homologous recombination nucleic acid molecule may be designed such that, upon homologous recombination, the endogenous PTB or PTB-T gene is mutated or otherwise altered but still encodes functional protein (e.g., the upstream regulatory region can be altered to thereby alter the expression of the endogenous PTB or PTB-T protein). In the homologous recombination nucleic acid molecule, the altered portion of the PTB or PTB-T gene is flanked at its 5' and 3' ends by additional nucleic acid sequence of the PTB or PTB-T gene to allow for homologous recombination to occur between the exogenous PTB or PTB-T gene carried by the homologous recombination nucleic acid molecule and an endogenous PTB or PTB-T gene in a cell, e.g., an embryonic stem cell. The additional flanking PTB or PTB-T nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas and Capecchi (1987) *Cell* 51:503). The homologous recombination nucleic acid molecule is introduced into a cell, e.g., an embryonic stem cell line, by for example electroporation, and cells in which the introduced PTB or PTB-T gene has homologously recombined with the endogenous PTB or PTB-T gene are selected (see, e.g., Li, et al. (1992) *Cell* 69:915). The selected cells may then be injected into a blastocyst of an animal (e.g., a mouse) to form aggregation chimeras (see, e.g., Bradley, In: Teratocarcinomas and Embryonic Stem Cells: A Practical Approach, Robertson, E. J. ed. (IRL, Oxford, 1987) pp. 113–152). A chimeric embryo may then be implanted into a suitable pseudopregnant female foster animal and the embryo brought to term. Progeny harboring the homologously recombined DNA in their germ cells may be used to breed animals in which all cells of the animal contain the homologously recombined DNA by germline transmission of the transgene. Methods for constructing homologous recombination nucleic acid molecules, e.g., vectors, or homologous recombinant animals are well-known (see, e.g., Bradley (1991) *Current Opin. Biotechnol.* 2:823–829; WO 90/11354; WO 91/01140; WO 92/0968; and WO 93/04169.

In a preferred embodiment of the invention, the stability of a CD154 mRNA is regulated by modulating the level or activity of PTB or PTB-T. In another preferred embodiment, any RNA sequence operatively-linked to a cis-acting element of CD154 3'-untranslated region is regulated by modulating the level or activity of PTB or PTB-T. RNA sequences which may be regulated in accordance with the invention include, but are not limited to, viral RNA sequences, ribozymes, antisense RNA, iRNA, mRNA, rRNa, tRNA, and snRNA. It should be understood that the stability of any length of RNA can be regulated including RNA molecules of 10 to 10000 or more bases in length. Typically, a fusion is produced between DNA molecules which encode the RNA sequence of interest and the cis-acting element of CD154 3'-untranslated region. However, RNA fusions are also contemplated. The fusion molecule is preferably produced by standard recombinant techniques. For example, a DNA molecule encoding the RNA sequence of interest is ligated to a DNA molecule encoding the cis-acting element and the resultant chimeric DNA molecule is expressed in a host cell to produce the fusion RNA. The DNA molecules are ligated to each other in a 5'-to-3' orientation such that, after ligation, the DNA molecule encoding the cis-acting element is 3' (i.e., downstream) of the DNA molecule encoding the RNA sequence of interest. The fusion molecule is than inserted into a suitable expression vector and transformed into a suitable host cell as provided herein.

A still further aspect of the invention is a method of identifying an agent which modulates the level or activity of PTB or PTB-T. The method provides contacting a test cell, which contains a reporter gene operatively-linked to a cis-acting element of a CD154 3'-untranslated region, with an agent and then detecting the expression of products of nucleic acid sequences encoding the reporter in the test cell. An agent which causes an increase or decrease in the expression of a product of the nucleic acid sequence encoding the reporter in the test cell when compared to a test cell not contacted with the agent, indicates that the agent modulates the level or activity of PTB or PTB-T in the test cell.

Test cells expressing a product of a nucleic acid sequence encoding a reporter which may be used in accordance with the method of the invention are preferably mammalian cells and most preferably human cells.

The reporter gene sequence(s) may be inserted into a recombinant expression vector as provided herein. More than one reporter gene may be inserted into the construct such that the test cells containing the resulting construct may be assayed by different means. The test cells which contain the nucleic acid sequences encoding the reporter and which express products of the nucleic acid sequences encoding the reporter may be identified by at least four general approaches; detecting DNA-DNA or DNA-RNA hybridization; observing the presence or absence of marker gene functions (e.g., resistance to antibiotics); assessing the level of transcription as measured by the expression of reporter mRNA transcripts in the host cell; and detecting the reporter gene product as measured by immunoassay or by its biological activity.

The test cells may be cultured under standard conditions of temperature, incubation time, optical density, plating density and media composition corresponding to the nutritional and physiological requirements of the cells. However, conditions for maintenance and growth of the test cell may be different from those for assaying candidate test compounds in the screening methods of the invention. Modified culture conditions and media are used to facilitate detection of the expression of a reporter molecule. Any techniques known in the art may be applied to establish the optimal conditions.

A reporter gene refers to any genetic sequence that is detectable and distinguishable from other genetic sequences present in test cells. Preferably, the reporter nucleic acid sequence encodes a protein that is readily detectable either by its presence, or by its activity that results in the generation of a detectable signal. A nucleic acid sequences encoding the reporter are used in the invention to monitor and report the stability of an RNA operatively-linked to a cis-acting element of a CD154 3'-untranslated region in test cells.

A variety of enzymes may be used as reporters including, but are not limited to, β-galactosidase (Nolan, et al. (1988) *Proc. Natl. Acad. Sci. USA* 85:2603–2607), chloramphenicol acetyltransferase (CAT; Gorman, et al. (1982) *Molecular Cell Biology* 2:1044; Prost, et al. (1986) *Gene* 45:107–111), β-lactamase, β-glucuronidase and alkaline phosphatase (Berger, et al. (1988) *Gene* 66:1–10; Cullen, et al. (1992) *Methods Enzymol.* 216:362–368). Transcription of the reporter gene leads to production of the enzyme in test cells. The amount of enzyme present may be measured via its enzymatic action on a substrate resulting in the formation of a detectable reaction product. The methods of the invention provide means for determining the amount of reaction product, wherein the amount of reaction product generated or the remaining amount of substrate is related to the amount of enzyme activity. For some enzymes, such as β-galactosidase, β-glucuronidase and β-lactamase, well-known fluorogenic substrates are available that allow the enzyme to covert such substrates into detectable fluorescent products.

A variety of bioluminescent, chemiluminescent and fluorescent proteins also may be used as light-emitting reporters in the invention. Exemplary light-emitting reporters, which are enzymes and require cofactor(s) to emit light, include, but are not limited to, the bacterial luciferase (luxAB gene product) of *Vibrio harveyi* (Karp (1989) *Biochim. Biophys. Acta* 1007:84–90; Stewart, et al. (1992) *J. Gen. Microbiol.* 138:1289–1300), and the luciferase from firefly, *Photinus pyralis* (De Wet, et al. (1987) *Mol. Cell. Biol.* 7:725–737).

Another type of light-emitting reporter, which does not require substrates or cofactors includes, but is not limited to, the wild-type green fluorescent protein (GFP) of *Victoria aequoria* (Chalfie, et al. (1994) *Science* 263:802–805), modified GFPs (Heim, et al. (1995) *Nature* 373:663–4; WO 96/23810), and the gene products encoded by the *Photorhabdus luminescens* lux operon (luxABCDE) (Francis, et al. (2000) *Infect. Immun.* 68(6):3594–600). Transcription and translation of these type of reporter genes leads to the accumulation of the fluorescent or bioluminescent proteins in test cells, which may be measured by a device, such as a fluorimeter, flow cytometer, or luminometer. Methods for performing assays on fluorescent materials are well-known in the art (e.g., Lackowicz, 1983, *Principles of Fluorescence Spectroscopy*, New York, Plenum Press).

For convenience and efficiency, enzymatic reporters and light-emitting reporters are preferred for the screening assays of the invention. Accordingly, the invention encompasses histochemical, calorimetric and fluorometric assays. An exemplary reporter construct, exemplified herein, contains the cis-acting element of a CD154 3'-untranslated region which regulates the stability of and therefore the translation (expression) of the reporter, luciferase.

Accordingly, the invention provides a method for screening for agents that modulate the level or activity of PTB or PTB-T comprising culturing a test cell which contains nucleic acid sequences encoding a reporter operatively-linked to a cis-acting element of a CD154 3'-untranslated region; adding a test agent to a point of application, such as a well, in the plate and incubating the plate for a time sufficient to allow the test agent to effect luciferase mRNA stability; detecting luminescence of the test cells contacted with the test agent, wherein luminescence indicates expression of the luciferase polypeptide in the test cells; and comparing the luminescence of test cells not contacted with the test agent. A decrease in luminescence of the test cell contacting the test agent relative to the luminescence of test cells not contacting the test agent indicates that the test agent causes a decrease in the level or activity of PTB or an increase in the level or activity of PTB-T in the test cell. An increase in luminescence of the test cell contacting the test agent relative to the luminescence of test cells not contacting the test agent indicates that the test agent causes an increase in the level or activity of PTB or a decrease in the level or activity of PTB-T in the test cell.

Agents which may be screened using the method provided herein encompass numerous chemical classes, though typically they are organic molecules, preferably small organic compounds having a molecular weight of more than 100 and less than about 2,500 daltons. Agents comprise functional groups necessary for structural interaction with proteins, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups. Agents may also be found among biomolecules including peptides, antibodies, saccharides, fatty acids, steroids, purines, pyrimidines, derivatives, structural analogs or combinations thereof.

Agents are obtained from a wide variety of sources including libraries of natural or synthetic compounds.

A variety of other reagents such as salts and neutral proteins may be included in the screening assays. Also, reagents that otherwise improve the efficiency of the assay, such as protease inhibitors, nuclease inhibitors, anti-microbial agents, and the like may be used. The mixture of components may be added in any order that provides for the requisite binding.

Alternatively, antibodies against the PTB or PTB-T polypeptides may serve as the agent to inhibit (antagonize) or stimulate (agonize) PTB or PTB-T activity. PTB or PTB-T polypeptides or epitope bearing fragments thereof may be used as immunogens to produce antibodies immunospecific for such polypeptides. Various techniques well-known in the art may be used routinely to produce antibodies (Kohler and Milstein (1975) *Nature* 256:495–497; Kozbor, et al. (1983) *Immunol. Today* 4:72; Cole, et al. (1985) In: Monoclonal Antibodies and Cancer Therapy, pp 77–96).

It is contemplated that agents which decrease the level or activity of PTB or increase the level or activity of PTB-T may be used to prevent or treat allograft rejection or inhibit CD40 activation by CD154 in a subject.

The invention is described in greater detail by the following non-limiting examples.

EXAMPLE 1

Preparation of Cytosolic and Polysomal Extracts

The Jurkat human T cell line was maintained in RPMI-1640 medium supplemented with 10% heat-inactivated fetal calf serum (HyClone, Logan, Utah) and 50 µg/ml gentamycin sulfate. Human PBL cells from volunteer donors were activated with phytohemagglutinin (PHA) (Murex Diagnostics Ltd., Dartford, England) at 1 µg/ml, a concentration found to give optimal proliferation and lymphokine preparation. Cytoplasmic preparations were performed using a standard method characterized for its lack of contamination by nuclear proteins (Hamilton, et al. (1993) *J. Biol. Chem.* 268:8881–87). Cytoplasmic lysates were prepared by washing the cells twice in ice-cold phosphate buffered saline. All reagents and subsequent steps were performed at 4° C. The cells were lysed by gentle resuspension in 1% TRITON® X-100 lysis buffer (50 µl/2×10$^7$ cells) containing 10 mM PIPES, pH 6.8, 100 mM KCl, 2.5 mM MgCl$_2$, 300 mM sucrose, 1 mM PEFABLOC® and 2 µg/ml each of leupeptin and pepstatin A before a 3 minute incubation followed by 3 minute centrifugation at 500×g. The supernatant was aliquoted and stored at −80° C. as the cytoplasmic fraction. Polysomes were prepared using a well-known method (Rigby, et al. (1999) supra). Human peripheral blood mononuclear cells from volunteer donors were homogenized in buffer A (10 mM Tris-HCl, pH 7.6, 1 mM potassium acetate, 1.5 mM magnesium acetate, 2 mM DTT, 2 µg/ml leupeptin and pepstatin A, and 2 mM PEFABLOC®) and nuclei removed by centrifugation. The supernatant was layered over a 30% sucrose cushion and followed by ultracentrifugation at 36,000 rpm for 4 hours at 4° C. The supernatant was removed as the S130 fraction and the pellet was resuspended in buffer A and stored in aliquots at −80° C. as the polysome fraction.

EXAMPLE 2

RNA Binding Assays

Human CD154 3'-UTR was generated by reverse transcriptase PCR (RT-PCR) using RNA isolated from PHA-activated (16 hour) PBL, using primers that generated products encoding CD154 nucleotides 12–986 and 468–835 of the human CD154 3'-UTR (Accession number gi 180123). Each primer set also introduced a SpeI restriction enzyme site at both ends. Following amplification, the PCR products were inserted into TOPO® 2.1 vector (INVITROGEN™, Carlsbad, Calif.) and confirmed by sequencing. CD154 12–986 and CD154 468–835 were excised from the TOPO® 2.1 vector with SpeI and ligated into the XbaI site of T7/T3 α-19 (GIBCO™ BRL, Gaithersburg, Md.) and confirmed by sequencing. T7/T3 CD154 483–814 del was generated by QUICKCHANGE® (STRATAGENE®, La Jolla, Calif.) deletion from the T7/T3 CD154 12–986. T7/T3 CD154 12–986 was linearized with KpnI or EcoRI to generate the 12–986 and 12–292 templates, respectively. T7/T3 CD154 486–835 was linearized with EcoRI. α-$^{32}$P-labeled mRNAs with specific activity of >$10^8$ cpm/µg RNA were prepared by in vitro transcription by T7 RNA polymerase in the presence of 50 µCi of α-[$^{32}$P]UTP (3000 Ci/mmole) (PERKIN-ELMER™ Life Sciences, Boston, Mass.) and 0.0125 mM UTP, and 2.5 mM ATP, GTP, and CTP (Roche Biochemicals, Indianapolis, Ind.).

RNA probes ($8 \times 10^4$ cpm; 3–14 fmole-calculated based on α-[$^{32}$P]UTP incorporation) were incubated with the specified amounts of cytoplasmic extract, nucleoplasmic extract or $A_{260}$ polysomes in 12 mM HEPES, pH 7.9, 15 mM KCl, 0.2 µM dithiothreitol, 0.2 µg/ml yeast tRNA, and 10% glycerol for 10 minutes at 30° C. UV cross-linking was performed at 4° C. using an UV STRATALINKER® 1800 (5 minutes, 3000 microwatts/cm$^2$) (STRATAGENE®, La Jolla, Calif.) followed by RNase digestion (10 units RNase T1 and 20 µg of RNase A) for 30 minutes at 37° C. (Rigby, et al. (1999) supra). The protein-RNA complexes were separated under denaturing conditions by 12% SDS-PAGE, dried, and analyzed by autoradiography. Protein-RNA complexes were immunoprecipitated by incubating the complexes with anti-PTB monoclonal antibody BB7 bound to protein-A SEPHAROSE® beads (Pharmacia AB, Uppsala, Sweden) for 2 hours at 4° C. Parallel immunoprecipitation was performed with the anti-hnRNP A2 monoclonal antibody, EF67 as a specificity control (Nichols, et al. (2000) Exp. Cell Res. 256:522–532). Beads were washed six times in 100 mM NaCl, boiled in SDS-PAGE loading buffer and resolved by 12% SDS-PAGE and analyzed by autoradiography.

Using a variety of RNA probes that varied in terms of which portion of the CD154 3'-UTR was contained, the binding regions for p50, p40 and p25 in calf thymus, Jurkat T cells, and human PBL were identified. The binding of the p50, p40, and p25 RNA binding proteins in these different extracts was mapped to nucleotides 468–835 of the human CD154 3'-UTR (SEQ ID NO:3).

EXAMPLE 3

Purification of PTB and PTB-Related Proteins

Purification of PTB and PTB-related proteins from calf thymus was performed as provided hereinafter and the fractions which contained p50 and p25 CD154 3'-UTR RNA binding activity as measured by UV crosslinking were followed throughout the purification. Radiolabeled RNA corresponding to 468–835 of the human CD154 3'-UTR was used to follow the binding activity of purified by column chromatography Proteins were purified as follows. Fresh calf thymus (1.2 kg) was obtained at a slaughterhouse, chopped into approximately one inch cubes and snap frozen in liquid nitrogen. The tissue was thawed overnight at 4° C. in buffer A (50 mM HEPES, pH 7.5, 25 mM KCl, 5 mM $MgCl_2$, 250 mM sucrose, 10 mM 2-mercaptoethanol, and 1 mM PEFABLOC®). All subsequent steps were performed at 4° C. using standard methods (Nichols, et al. (2000) supra). The tissue was ground in a blender in three liters buffer A and subsequently the crude homogenate was passed successively through 2, 4, and 8 layers of cheesecloth. The suspension was centrifuged at 1800×g for 7 minutes. The supernatant was transferred to clean tubes as the cytoplasmic fraction. The nuclear pellet was resuspended in two liters extraction buffer (250 mM sucrose, 400 mM NaCl, 50 mM HEPES pH 7.5) and subsequently centrifuged at 8500 rpm in a GS3 rotor for 10 minutes. The supernatant was saved as the nucleoplasmic extract and sequentially subjected to 25%, 50% and 75% ammonium sulfate precipitation. The ammonium sulfate precipitates were resuspended in dialysis buffer (50 mM NaCl, 20 mM HEPES, pH 7.5, 2 mM EDTA, 10% w/v glycerol, 10 mM 2-mercaptoethanol, and 1 mM PEFABLOC®) before 2×2 hour dialysis at 4° C.

Fractions were analyzed for the presence of CD154 3'-UTR RNA binding proteins. The nuclear 50% ammonium sulfate fraction (120 mL) was applied to 130 mL DEAE-SEPHACEL® (Sigma-Aldrich, St. Louis, Mo.) column. The flow through was collected and the column washed with 500 mL of binding buffer (20 mM HEPES, pH 7.5, 10 mM KCl, 0.2 µM DTT, 10% glycerol, and 1 mM PEFABLOC®). Proteins were eluted with 0.1, 0.3, 0.5 and 1 M KCl and analyzed for RNA binding activity. The flow through and 0.1 M elution fraction were combined and passed over a carboxymethyl cellulose (CMC) column and eluted with 0.1, 0.3, 0.5, and 1 M KCl step-gradient. The 0.3 M elution was dialyzed against poly U SEPHAROSE® binding buffer (12 mM HEPES, pH 7.5, 15 mM KCl, 1 µg/mL yeast tRNA, 0.2 µM DTT, 100 µM PEFABLOC® and 10% glycerol) and applied to a 2 mL poly (U) Sepharose® column, washed and eluted. Specified elutions were resolved by 12% SDS-PAGE, and the p25 and p50 COOMASSIE® Blue stained bands were excised and identified. The p50 was identified by MS/MS analysis of the tryptic digest on a Q-TOF mass spectrometer. The p25 peptide was identified by internal amino acid sequencing of a tryptic digest.

EXAMPLE 4

Immunoblotting

Following resolution by 12% SDS-PAGE and electrotransfer to nitrocellulose, blots were blocked overnight at 25° C. in Tris-buffered saline/0.05% TWEEN®-20 (TBS-T) containing 3% bovine serum albumin before incubating 1 hour at 25° C. with a BB7 hybridoma supernatant (diluted 1:2000) or affinity-purified rabbit antisera specific for the N-terminal 13 amino acids of PTB (diluted 1:200) in TBS-T (1% BSA). Blots were then washed, incubated with 1:10000 dilution of goat-anti-mouse-HRP secondary antibody for 1 hour at room temperature, washed five times with TBS-T and visualized using the SUPERSIGNAL® chemiluminescence substrate (Pierce, Rockford, Ill.).

EXAMPLE 5

Cloning of the p25/PTB-T

The p25/PTB-T was cloned by RT-PCR amplification using upper and lower primers corresponding to the 5'-UTR and 3'-UTR of human PTB. For the upper primer, nucleotides 66–85 (5'-CCCGCGGTCTGCTCTGTGTG-3'; SEQ ID NO:7) were used, while the lower primer utilized nucleotides 1816–1839 (5'-AATCTCTCGGCGGCTAGGT-CACT-3'; SEQ ID NO:8). RNA from two different donor PHA-activated PBL as well as the Jurkat human T cell line was isolated, reverse-transcribed with SUPERSCRIPT II™ reverse transcriptase (INVITROGEN™, Carlsbad, Calif.) using oligo-d(T) (INVITROGEN™, Carlsbad, Calif.), and PCR-amplified using Taq DNA polymerase (Roche Biochemicals, Indianapolis, Ind.). A 700 bp band was resolved by agarose gel electrophoresis, excised, cloned into TOPO® 2.1 (INVITROGEN™, Carlsbad, Calif.), and sequenced. Identical sequences of PTB-T were seen in multiple clones derived from each RT-PCR. PTB-T was then PCR-amplified from TOPO® 2.1/PTB-T and TA cloned into pcDNA3.1 (INVITROGEN™, Carlsbad, Calif.) and sequenced to confirm that no errors were introduced during amplification. In vitro transcription and translation of [$^{35}$S]-methionine-labeled PTB-T was performed using pcDNA3.1 PTB-T vector and PROTEINSCRIPT™ II (AMBION™, Inc., Austin, Tex.). Labeled proteins were resolved by 12% SDS-PAGE and visualized by autoradiography. The pTRI-Xef1α cDNA, which encodes a ~50 kD protein, was the positive control (AMBION™, Inc., Austin, Tex.).

EXAMPLE 6

Transient Transfection of Cell Lines

PTB was released from pRC/PTB (hnRNP I) vector with HindIII and ligated into the HindIII site in pcDNA 3.1 to yield pcDNA3.1-PTB. Luciferase reporter constructs were generated by digesting TOPO® 2.1/CD154 3'-UTR 12–986 with BamHI and XhoI to release CD154 3'-UTR 104–986; ligating into BamHI and XhoI of pcDNA3.1 Zeo(+) (INVITROGEN™, Carlsbad, Calif.); and confirming by sequence analysis. The cDNA encoding firefly luciferase was released from pGL3-control vector (PROMEGA®, Madison, Wis.) by XbaI and HindIII digestions, gel purified, and ligated into the BamHI site of pcDNA3.1/CD154 104–986 to yield pcDNA3.1/LUC/CD154 104–986. Digestion of pcDNA3.1/LUC/CD154 104–986 with BamHI and XhoI resulted in the release of the CD154 3'-UTR; religation yielded pcDNA3.1/LUC. The pcDNA3.1/LUC/CD154 468–835 expression plasmid was generated by digesting TOPO® 2.1/CD154 468–835 with BamHI and XhoI and ligating gel purified insert into the pcDNA3.1/LUC/CD154 104–986 that had been digested with BamHI and XhoI to remove CD154 104–986. Deletion constructs were generated by QUIKCHANGE® (STRATAGENE®, La Jolla, Calif.) deletion from TOPO® 2.1/CD154 12–986, released by BamHI/XhoI digestion and ligated into the XbaI site of pcDNA 3.1/LUC. For generation of tetracycline-repressible luciferase expression, inserts containing the CD154 3'-UTR were released by BamHI/EcoRV digestion from TOPO® vectors provided above and cloned into the EcoRV site downstream of the luciferase coding region in the pTRE-Luc vector (Clontech, Palo Alto, Calif.). Each vector was verified by sequencing at least twice in each direction.

Transient transfections were performed using 2×10$^6$ Jurkat or 10$^6$ HeLa cells with 0.1 µg luciferase vectors plus 6 µl LIPOFECTAMINE™ (GIBCO™ BRL, Gaithersburg, Md.) in 0.5 mL RPMI for 2.5 hours at 37° C., 5% CO$_2$, after which 1 mL RPMI+20% FCS was added. After 20 hours, cells were lysed and luciferase activity determined using Luciferase Reporter Assay (PROMEGA®, Madison, Wis.) and luminometry. In each experiment, data represent the CD154 3'-UTR-specific effect by dividing the mean luciferase activity from triplicate transfections of pcDNA3.1/LUC/CD154 3'UTR-containing expression plasmids by that obtained from cells transfected with the pcDNA 3.1 LUC vector, which was assigned a value of 100%. In PTB and PTB-T overexpression experiments, one µg of pcDNA3.1 PTB-T, pcDNA3.1-PTB, or an empty vector control was used with 0.1 µg of the luciferase expression plasmids that either lacked or contained the CD154 3'-UTR and mean luciferase activity determined. In these experiments, the percent inhibition of CD154 3'-UTR-dependent luciferase expression seen with each vector was calculated and then divided by the inhibition seen with the empty control vector, which was assigned a value of 100%.

EXAMPLE 7

Transient Transfection of Primary CD4+ T Cells

Primary human CD4 T cells (>95% purity) were isolated from PBL by negative selection (StemCell Technologies, Vancouver, B.C.) and transiently transfected using well-known methods (Cron, et al. (1997) *J. Immunol. Methods* 205:145–50). After overnight culturing with an equivalent number of irradiated (3300 rads) syngeneic whole blood mononuclear cells in 1 µg/ml of PHA, CD4 T cells were isolated and subjected to electroporation 19.5 hours post-PHA stimulation. Five million CD4 T cells were transiently transfected with plasmid DNA in 250 µl of media in 0.4 cm cuvettes at 250 V, 950 µF using a GENE PULSER® (BIO-RAD®, Hercules, Calif.). Two micrograms of either pcDNA3.1/LUC/CD154 104–986 or pcDNA3.1/LUC cDNA was co-transfected with 2 µg of expression vector (pcDNA 3.1, pcDNA 3.1 PTB or pcDNA3.1 PTB-T) along with 1 µg of a *Renilla* luciferase expression control vector, pRL-null (PROMEGA®, Madison, Wis.). Cells were rested for 2 hours and 1 million cells per well were stimulated in vitro with PMA (25 ng/ml) and ionomycin (1.5 µM) or media alone for 6 hours at 37C. Cells were washed and lysed, and luciferase activity was determined using a Dual Luciferase assay kit (PROMEGA®, Madison, Wis.) and a LB9507 luminometer (EG&G Wallac, Bad Wildbad, Germany). Data was analyzed in duplicate and corrected for transfection efficiency based on *Renilla* luminescence (Cron, et al. (2000) *Clin. Immunol.* 94:179–91).

EXAMPLE 8

Northern/RT-PCR Light Cycler RNA Analysis

Jurkat cells were transiently transfected as described and total cellular RNA was extracted by acid guanidinium-phenol-chloroform extraction (Chomczynski and Sacchi (1987) *Anal. Biochem.* 162:156–159) modified by increasing the 2-mercaptoethanol (Sigma-Aldrich, St Louis, Mo.) from 0.1 M to 0.7 M in the 5 M guanidinium thiocyanate (Fluka, Switzerland) denaturing solution. RNA was size fractionated by formaldehyde-agarose gel electrophoresis and blotted to HYBOND™-N nylon membrane (Amersham Corp., Arlington Heights, Ill.) in 20×SSC, and baked under vacuum at 80° C. for 2 hours. The northern blot was sequentially hybridized with an end-labeled luciferase primer (5'-GGTACTTCGTCCACAAACACAACTCC-3'; SEQ ID NO:9) and oligo-labeled HLA-B7 cDNA and visualized by autoradiography, with quantification performed by phosphorimaging using the PHOSPHORIMAGER™ 445 SI (MOLECULAR DYNAMICS™, Sunnyvale, Calif.). A separate transfection was analyzed by real time PCR. Total cellular RNA was extracted using RNEASY® Kit (QIAGENO, Valencia, Calif.) and poly(A)+ RNA isolated using OLIGOTEX® beads (QIAGEN®, Valencia, Calif.). Poly(A)+ RNA was digested with DNase I (AMBION®, Inc., Austin, Tex.) prior to reverse transcribing with oligo dT and SUPERSCRIPT II™ RT (INVITROGEN™, Carlsbad, Calif.). Reverse transcriptions were analyzed for luciferase transcripts using 5'-GGTGGCTCCCGCTGAATTGG-3' (SEQ ID NO:10) (upper primer) and 5'-CCGTCATCGTCTTTCCGTGC-3' (SEQ ID NO:11) (lower primer) and SYBER® Green PCR Core Reagents (APPLIED BIOSYSTEMS™, Foster City, Calif.) by real time PCR using an ICYCLER™ (BIO-RAD®, Hercules, Calif.). Each RT reaction was simultaneously examined for GAPDH transcript as a control. The luciferase/GAPDH transcript ratio was calculated for each sample, based on the manufacturer's instructions. For studies of mRNA stability, TET-OFF™ HeLa cells (Clontech, Palo Alto, Calif.) were obtained and used according to manufacturer's instructions. Transient transfection of these cell was as described above. Cells were allowed to recover overnight, then treated with Doxycyline (1 µg/ml) to shut off transcription for specified times. RNA extraction and analysis was performed as described above.

What is claimed is:

1. An isolated polypyrimidine tract protein isoform comprising SEQ ID NO: 1.

* * * * *